US008715644B2

(12) United States Patent
Guyonnet et al.

(10) Patent No.: US 8,715,644 B2
(45) Date of Patent: May 6, 2014

(54) METHOD FOR DECREASING BORBORYGMI BY ADMINISTERING A BIFIDOBACTERIUM BACTERIA

(75) Inventors: Denis Guyonnet, Levallois-Perret (FR); Stefan Jakob, Saint Arnoult-en-Yvelines (FR); Armelle Schlumberger, Paris (FR)

(73) Assignee: Compagnie Gervais Danone, Paris (FR)

( * ) Notice: Subject to any disclaimer, the term of this patent is extended or adjusted under 35 U.S.C. 154(b) by 103 days.

(21) Appl. No.: 12/993,900

(22) PCT Filed: May 26, 2009

(86) PCT No.: PCT/EP2009/056344
§ 371 (c)(1),
(2), (4) Date: Feb. 10, 2011

(87) PCT Pub. No.: WO2009/150036
PCT Pub. Date: Dec. 17, 2009

(65) Prior Publication Data
US 2011/0129451 A1    Jun. 2, 2011

(30) Foreign Application Priority Data

May 26, 2008  (EP) .................................. 08305201
Jun. 5, 2008   (EP) .................................. 08305234

(51) Int. Cl.
*A01N 63/00*   (2006.01)
*A61F 2/00*    (2006.01)
*A61K 31/74*   (2006.01)
*A01N 65/00*   (2009.01)

(52) U.S. Cl.
USPC ....... 424/93.4; 424/442; 424/78.01; 424/93.1

(58) Field of Classification Search
None
See application file for complete search history.

(56) References Cited

U.S. PATENT DOCUMENTS 7,008,785 B2 * 3/2006 Antoine et al. ............... 435/243
2004/0241815 A1 * 12/2004 Sato et al. .................... 435/136
2010/0285175 A1 * 11/2010 Hendriksen et al. ........... 426/42

FOREIGN PATENT DOCUMENTS

WO    WO 02/02800    1/2002

OTHER PUBLICATIONS

Guyonnet et al. "Effect of a fermented milk containing Bifidobacterium animalis DN-173 010 on the health-related quality of life and symptoms of irritable bowel syndrome in adults in primary care: a multicentre, randomized, double-blind, controlled trial." Alimentary Pharmacology & Therapeutics 26, 475-486 (2007).*
Kajander et al. "A probiotic mixture alleviates symptoms in irritable bowel syndrome patients: a controlled 6-month intervention." Aliment Pharmacol Ther 2005: 22; 387-394.*
Guyonnet et al. "Effect of a fermented milk containing Bifidobacterium animalis DN-173 010 on the health-related quality of life and symptoms in irritable bowel syndrome in adults in primary care: a multicentre, randomized, double-blind, controlled trial" Alimentary Pharmacology & Therapeutics, 475-486, (2007).*

(Continued)

*Primary Examiner* — Blaine Lankford
*Assistant Examiner* — Lauren K Van Buren
(74) *Attorney, Agent, or Firm* — Vedder Price P.C.; Thomas J. Kowalski

(57) ABSTRACT

The present invention relates to a method for decreasing borborygmi in a subject by administering a probiotic, preferably a bacteria of the *Bifidobacterium* genus, said method being on one aspect of the invention a non therapeutic method.

17 Claims, 3 Drawing Sheets

(56) References Cited

OTHER PUBLICATIONS

Manufacturing yogurt and fermented milks/editor Ramesh C. Chandan, 2006 Blackwell Publishing.*

Guyonnet et al. "Effect of a fermented milk containing Bifidobacterium animalis DN-173 010 on the health-related quality of life and symptoms in irritable bowel syndrome in adults in primary care: a multicentre, randomized, double-blind, controlled trial" Alimentary Pharmacology & Therapeutics, 475-486, ((2007).*

Search Report, Written Opinion and International Preliminary Report on Patentability received in PCT/EP2009/056344, (Jan. 4, 2003; Mar. 27, 2003; Nov. 6, 2013).

Guyonnet et al., "Effect of a fermented milk containing *Bifidobacterium animalis* DN-173 010 on the health-related quality of life and symptoms in irritable bowel syndrome in adults in primary care: a multicentre, randomized, double-blind, controlled trial", *Alimentary Pharmacology & Therapeutics,* vol. 26, pp. 475-486 (2007).

Kajander et al., "A probiotic mixture alleviates symptoms in irritable bowel syndrome patients: a controlled 6-month intervention", *Alimentary Pharmacology & Therapeutics,* vol. 22, pp. 387-394 (2005).

Kajander et al., "Clinical trial: multispecies probiotic supplementation alleviates the symptoms of irritable bowel syndrome and stabilizes intestinal microbiota" *Alimentary Pharmacology & Therapeutics,* vol. 27, pp. 48-57 (2008).

* cited by examiner

METHOD FOR DECREASING BORBORYGMI BY ADMINISTERING A BIFIDOBACTERIUM BACTERIA

The present invention relates to a method for decreasing borborygmi in a subject by administering a bacteria of the *Bifidobacterium* genus, said method being on one aspect of the invention a non therapeutic method.

Borborygmi during the day are normal for healthy individuals and are audible bowel sounds (15). Borborygmi are caused by the muscular contractions of peristalsis, the process that moves the contents of the stomach and intestines downward. Peristalsis is the rippling motion of muscles in the digestive tract. In the stomach, this motion mixes food with gastric juices, turning it into a thin liquid. Borborygmi, especially in the morning and after meals, are, for a lot of people, an everyday or punctual discomfort that they would like to make disappear or at least to reduce.

Borborygmi, like other gastrointestinal symptoms such as bloating, abdominal pain or flatulence, are generally more frequent and severe in irritable bowel syndrome (IBS) (1).

IBS is a functional bowel disorder in which abdominal pain or discomfort is associated with defecation or change in bowel habit and with features or disordered defecation (1).

Thus, there is need for means to reduce partially or totally small frequency borborygmi for healthy subject but also to reduce partially or totally more frequent borborygmi.

It has been shown that the use of certain probiotic preparations, containing bacteria such as propionic bacteria, lactobacilli and/or bifidobacteria, makes it possible to modify the flora in the colon of certain patients (8, 9, 9bis). Moreover, in both man and animal models, a number of probiotics have been shown to modify gastrointestinal contractility or excessive flatulence, meteorism, or abdominal pain (10).

A long term (5-month) randomized double blind placebo-controlled study has shown positive effects of a mixture of 4 lyophilized probiotics (*Lactobacillus rhamnosus* GG, *L. rhamnosus* LC705, *Bifidocbacterium animalis* Bb12 and *Propionibacterium freudenreichii* ssp. *Shermani* JS) (11). In 86 subjects suffering from IBS and fulfilling Rome II criteria, this probiotic combination alleviates gastrointestinal symptoms during the last month as assessed by a reduction of a global score. However, non significative results concerning borborygmi have been shown.

An another long-term (6-month), randomised, double blind, placebo-controlled study has shown positive effects of a mixture of 4 lyophilized probiotics (*Lactobacillus rhamnosus* GG, *L. rhamnosus* LC705, *Bifidocbacterium breve* Bb99 and *Propionibacterium freudenreichii* ssp. *Shermani* JS), administered in a capsule (14). In 103 subjects suffering from IBS and fulfilling Rome I and II criteria, this probiotic combination alleviates gastrointestinal symptoms during the last month as assessed by a reduction of a global score and improvement of borborygmi starting from the fourth month of treatment (months 4, 5, 6). However, non significative results concerning borborygmi have been shown during the 3 first months of the study, which was concerning IBS patients.

Thus, to date, no study has shown a positive effect of using a probiotic on borborygmi, especially on healthy subjects, and more specifically during a short period time of administration of less than 3 months.

Surprisingly, it has been found that administration of at least about $1 \times 10^9$ cfu of a bacteria chosen in the group of bacteria of the *Bifidobacterium* genus per day during at least 15 days can reduce significantly borborygmi in a healthy subject.

An object of the present invention is therefore a method for decreasing borborygmi in a subject comprising the step of administering to said subject at least about $1 \times 10^9$ cfu of a bacteria chosen in the group of bacteria of the *Bifidobacterium* genus per day. More preferably, said method is for decreasing borborygmi in a subject in less than 3 months of administration of said bacteria.

DEPOSITS

The bacteria *Bifidobacterium animalis* subspecies *lactis* was deposited on Jun. 20, 2000, at the Collection Nationale de Cultures de microorganismes (CNCM), having an address Institut Pasteur, 25 rue du Docteur Roux F-75724 PARIS Cedex 15 France, under deposit accession number CNCM I-2494 pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

In a preferred embodiment of the invention said bacteria is administered during at least 15 days.

The term "borborygmus" or "borborygmi" in plural is intended to mean rumbling noises from the abdominal area which are audible bowel sounds (15).

The term "administering" is intended to mean "administering orally" i.e. that the subject will orally ingest a bacteria according to the present invention or a composition comprising the bacteria according to the present invention, or "administering directly" i.e. that a bacteria according to the present invention or a composition comprising the bacteria according to the present invention will be directly administered in situ, in particular by coloscopy, or rectally via suppositories.

The expression "healthy subjects" is intended to mean "global population of people without any diagnosed gastrointestinal disorders and especially functional bowel disorders such as Irritable Bowel Syndrome".

Oral administration of composition comprising the bacteria according to the present invention may be in the form of gelatin capsules, of capsules, of tablets, of powders, of granules or of oral solutions or suspensions.

In a preferred embodiment of the invention, said composition is a food composition which can be used in the production of new foods or food ingredients as defined in EC Regulation No. 258/97, and in particular in the manufacture of functional foods. A food may be considered to be functional if it is demonstrated satisfactorily that it exerts a beneficial effect on one or more target functions in the organism, beyond the usual nutritional effects, improving the state of health and of well-being and/or reducing the risk of a disease (12).

In a preferred embodiment of the invention, said bacteria is administered in the form of a dairy product. In particular, the dairy product is a fermented dairy product and more particularly the fermented dairy product is a yoghourt.

In a preferred embodiment of the invention, said fermented dairy product or said yoghourt comprises *Lactobacillus bulgaricus* and/or *Streptococcus thermophilus*, preferably both.

In a preferred embodiment of the invention, said fermented dairy product or said yoghourt does not comprise *Lactobacillus rhamnosus*, and/or *Propionibacterium freudenreichii*.

Said composition may in particular constitute a probiotic packaged, for example, in the form of a capsule or a gelatin capsule.

In another preferred embodiment of the invention, said composition is a pharmaceutical composition, also combined with a pharmaceutically acceptable carrier, which may comprise excipients.

The term "pharmaceutical composition" is intended to mean "drug" or "OTC (Over The Counter)".

According to the invention, the decrease of borborygmi of the subject is a decrease of at least about 10% of the frequency of borborygmi episodes, as an example about 15, 17 or 20%.

Preferably, the decrease of borborygmi of the subject is at least about 25% of the frequency of borborygmi episodes as an example 30, 35 or 40%.

More preferably, the decrease of borborygmi of the subject is at least about 45% of the frequency of borborygmi episodes as an example 50, 55 or 60%.

According to a preferred embodiment of the invention, the decrease of at least about 10% of the frequency of borborygmi episodes of the subject is obtained after 15 days of administration of bacteria, more preferably, the decrease of at least about 20% of the frequency of borborygmi episodes of the subject is obtained after 4 weeks of administration of bacteria.

According to the invention, the decrease of borborygmi of the subject is a decrease of at least about 20% of the frequency of borborygmi episodes.

Preferably, the decrease of borborygmi of the subject is at least about 50% of the frequency of borborygmi episodes.

For example, a subject having borborygmi every day (at least of borborygmi episode/day will, after administration of at least about $1\times10^9$ cfu per day of a bacteria chosen in the group of bacteria of the *Bifidobacterium* genus, preferably after 15 days of administration, had borborygmi 2 to 3 days/week (2 to 3 days/week with at least one episode of borborygmi).

The bacteria is chosen in the group of bacteria of the *Bifidobacterium* genus and is considered as a probiotic.

The term "probiotics" is intended to mean dietary supplements containing potentially beneficial bacteria or yeasts. According to the currently adopted definition by FAO/WHO, probiotics are: 'Live microorganisms which when administered in adequate amounts confer a health benefit on the host'. Lactic acid bacteria are the most common type of microbes used. Lactic acid bacteria have been used in the food industry for many years, because they are able to convert sugars (including lactose) and other carbohydrates into lactic acid. This not only provides the characteristic sour taste of fermented dairy foods such as yogurt, but also by lowering the pH may create fewer opportunities for spoilage organisms to grow, hence creating huge health benefits on preventing gastrointestinal infections. Strains of the genera *Lactobacillus* and *Bifidobacterium*, are the most widely used probiotic bacteria.

Probiotic bacterial cultures are intended to assist the body's naturally occurring gut flora to reestablish themselves. They are sometimes recommended by doctors and, more frequently, by nutritionists, after a course of antibiotics, or as part of the treatment for gut related candidiasis. Claims are made that probiotics strengthen the immune system to combat allergies and other immunal diseases.

Preferably the bacteria is chosen in the group of *Bifidobacterium animalis* subspecies *lactis*, *Bifidobacterium animalis*, *Bifidobacterium infantis* and *Bifidobacterium lactis* species.

More preferably, the bacteria according to the present invention is a *Bifidobacterium animalis* subspecies *lactis*.

More preferably the bacteria according to the present invention is a *Bifidobacterium animalis* subspecies *lactis* deposited under the number I-2494 at CNCM on Jun. 20, 2000. This strain is known under the code DN-173 010 and is protected, with its use as glycosylation modulator of intestinal cell surface, by European Patent EP 1 297 176.

According to new taxonomy, now the strain is classified as *B. animalis* subspecies *lactis* (16) and can be commonly named *B. lactis*.

In a preferred embodiment of the invention, about $1\times10^{10}$ cfu of bacteria per day is administered to the subject during at least 15 days, preferably at least 28 days, more preferably at least 4 weeks.

More preferably, $1,25\times10^{10}$ cfu of bacteria is administered to the subject two times per day during at least 15 days, preferably at least 28 days, more preferably at least 4 weeks.

According to the invention, the subject can be a child, an adult or an elderly, preferably an adult.

In a preferred embodiment of the invention the subject is a female.

Indeed it has been shown that female subjects has predisposition for increase of irritable bowel syndrome (1, 13).

In a preferred embodiment, the subject has or is subjected to borborygmi.

According to an embodiment of the invention, the method is a non therapeutic method.

The purpose of said non therapeutic method is to decrease borborygmi of healthy subjects of the population, in particular after meals. Preferably, said non therapeutic method is to decrease the frequency of borborygmi of said subjects.

The Deposits with CNCM (Collection Nationale de Cultures de Microoorganismes), under deposit accession number 1-2494 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

EXAMPLES

I. Material and Methods

I-A Study Population

Figure 1:
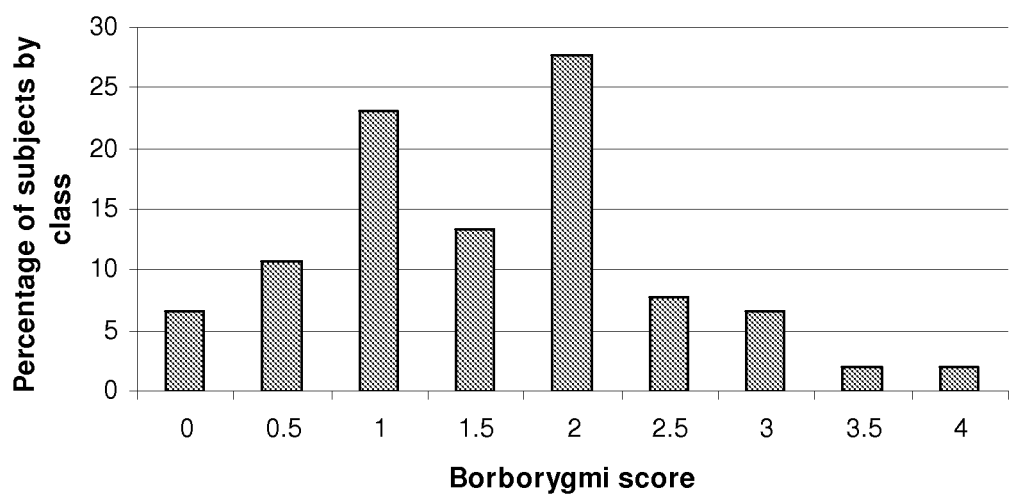
FIG. 1: baseline distribution of the frequency of borborygmi: values are expressed as percentage of subjects by class (0=never; 1=one time per week; 2=two to three days per week; 3=four to six days per week; 4=everyday during the week).

The study was mono-centre, randomized, double blind, controlled, in two parallel-groups (test group (100 patients) and control group).

The study was carried out in 197 healthy women with minor digestive symptoms aged 18-60 years, without a diagnosis of Gastro-intestinal disorders and especially functional bowel disorders, aged from 18 to 60 years.

Inclusion Criteria

Female free-living subject aged from 18 to 60 years.
Subject with a body mass index between 18 and 30, bounds included.
Subject with minor digestive symptoms as defined by score between 8 and 16 (bounds included) or at least one digestive symptom with a score ≥4 according to the following screening questionnaire of frequency of digestive symptoms.

Screening Questionnaire of Frequency of Digestive Symptoms:

The 4 following questions are asked to a subject:
1. In the last month, how often did you have discomfort or pain anywhere in your abdomen?
2. In the last month, how often did you have bloating?
3. In the last month, how often did you have flatulence/passage of gas?
4. In the last month, how often did you have borborygmi/rumbling stomach?

For each question, the subject can answer with one of 5 proposed answers, each answer giving a score: "Never" (score=0), "One day a month" (score=1), "Two to three days a month" (score=2), "One day a week" (score=3), "More than one day a week" (score=4) and "Every day"(score=5).

The subject is included in the study if she has a global score for questions 1-4 between 8 and 16 (bounds included); or at least one symptom (1-4) with a score ≥4.

Subject with stool frequency between 3 and 21 bowel movements per week (bounds included).

To obtain this stool frequency, the subject has to answer to the following question: In the last month, how many bowel movement you have per week on average?

For non-menopausal women: subject using contraceptive methods.

Fertile women who are not currently taking oral birth control pills (at least 1 full monthly cycle prior to study medication administration and continued until 1 month following the last dose of study medication) should be using or complying with one of the other medically approved methods of contraception such as, but not exclusively, one of the following: a) Intra-uterine device (IUD); b) Double barrier methods (such as condoms and spermicide); c) Abstinence, when in the opinion of the investigator, their occupation or life style gives sufficient evidence that abstinence will be maintained throughout the study and for 1 month thereafter. In the case of abstinence, it should be recorded in the source documents that the subject was appropriately counselled."

Subject having given written consent to take part in the study.

Subject with usual consumption of dairy products and ready to consume 2 pots of study product per day.

Non-Inclusion Criteria

Subject with a diagnosis of Irritable Bowel Syndrome (IBS) or other functional bowel disease (constipation, diarrhoea . . . ).

Subject checked by a general practitioner or gastroenterologist for digestive symptoms of the lower tract (colon and small intestine).

Subject with known organic disease, including an inflammatory bowel disease, a benign or malign tumour of intestine or colon and significant systemic disease.

Subject under prescription for medication for digestive symptoms such as anti-spasmodic, laxatives and anti-diarrheic drugs.

Subject having taken antibiotics in the last 4 weeks.

Change of dietary habits within the preceding 4 weeks (for instance start of a diet high in fibres).

Subject undergoing general anaesthesia in the preceding 4 weeks.

Pregnant subject or subject planning to become pregnant during the study; breast-feeding subject.

Subject with known lactose intolerance or immunodeficiency.

Subject with known allergy to product component (milk protein for example).

Subject involved in any other clinical study within the preceding month or in exclusion period after another clinical study.

Subject in a situation, which in the investigator's opinion could interfere with optimal participation in the present study or could constitute a special risk for the patient.

Subject not able to understand and/or to answer to the questions.

Throughout the study, the subjects had not to consume any probiotic or fermented dairy products other than those provided. They were encouraged to continue with all the other aspects of their dietary and physical exercise habits.

Randomisation Criteria

Subject having a mean composite score of frequency of digestive symptoms (bloating, abdominal pain/discomfort, flatulence/passage of gas and borborygmi/rumbling stomach) >2 and 12 during the run-in period.

Subject with mean stool frequency comprises between 3 and 21 bowel movements per week (bounds included) during the run-in period.

No consumption of antibiotics during the run-in period.

I-B Study Conduct

Run-in Period

Subjects willing to participate to this study have been invited to have a first visit (inclusion visit V1) at the clinical unit to check the inclusion and non-inclusion criteria. The subjects also had to fill in a screening questionnaire to determine the frequency of their digestive symptoms. To be included in the study, the subject must have a minimal score ≥8 or at least one digestive symptom with a score ≥4 (positive screening questionnaire). During this visit, the investigator has noted medical and surgical history including concurrent disease and treatment. Current medication use for gastrointestinal symptoms has been explicitly documented.

The subjects meeting all eligibility criteria have been entered in the 2-week run-in period.

These subjects have been provided with a subject diary to be filling in everyday during the 2-week run-in period. They also have received dietary recommendations (i.e. the exclusion of other fermented dairy products and probiotics) to be followed during the entire study. This run-in period before the start of the consumption of the fermented dairy products is necessary to collect baseline data for outcome parameters in order to capture the natural variation of the digestive symptoms and to verify that subjects have a minimum of digestive symptoms as defined in the randomisation criteria. This period has been used to homogenize the dietary consumption of fermented dairy products and probiotics.

Double-Blind Period

During the 4 weeks of product consumption in double-blind, all subjects have been asked to follow the dietary information provided. Subjects have been required to record daily and weekly information that will be used to measure the effects of the fermented dairy product Activia®.

The subjects had to daily record:
Number of study products consumed
Number and type of non-authorised products consumed
The subjects had to weekly record:
Frequency of digestive symptom: borborigmy/rumbling stomach I-C Description of Product Administration
Products The test product is the fermented dairy product Activia® marketed by Danone and containing alive bacteria. It contains a specific organism, *Bifidobacterium animalis* DN-173 010 ($1.25 \times 10^{10}$ colony forming unit (cfu) per pot), combined with two traditional yoghurt starters, *Streptococcus thermophilus* and *Lactobacillus bulgaricus* ($1.2 \times 10^9$ cfu/pot).

The control product is a milk-based non-fermented dairy product (without probiotics) and with a low content of lactose (<4 g/pot), with appearance, texture and taste close to that of the test product.

Both test and control products are not flavoured. Each serving (one pot) of either test or placebo control product contained 125 g.

Methods of Administration

Subjects have begun consumption of the study product following randomisation, the morning of the following day of the randomisation visit. The subjects have consumed 2 pots of the test or control product daily throughout the entire 28 days period of consumption in double-blind (until end of week 4) according to the randomisation list (except the first and last days, where they have consumed only one product, respectively at the dinner and at the breakfast). The products must be consumed within a meal twice a day, preferably once at breakfast and once at dinner. In the case of subjects forgetting to eat the product they have been advised to consume it with their next meal.

The subjects have been authorised to consume the products with sugar, marmalade, jam, fruits and cereals for instance. The products have to be consumed at fresh temperature (not possible to heat them).

Products and Treatments Authorized and Forbidden During the Study

During the entire duration of the study, subjects have been required to follow dietary recommendations. They should avoid the ingestion of any other fermented dairy products such as yogurts or probiotics containing products (e.g. Yakult, Actimel® . . . ) and any tablets, pills, powders or other food supplements containing probiotics other than those provided. All cheeses and other milk products can be included and thus consumed. The subjects have also been required to avoid making any significant changes to their usual diet during the study period (i.e. no changes to the usual amount of fibre, no commencement of a weight loss diet etc).

The objective of these dietary recommendations is to limit confounding factors in the evaluation of the product effect.

During all the study, all drugs are authorised except the antibiotics. In the case of antibiotics consumption, the subject would have been withdrawn from the study.

In case of any drug consumption, the subject would have been asked to complete her subject diary with the name, the dose and the intake dates of the medicine consumed. The subjects would have been advised to contact the investigator or the study nurse for recommendation about the treatments to be consumed.

II—Evaluation of Product Effect

Frequency of borborygmi/rumbling stomach, self-evaluated by subjects with a 5-points Likert scale (weekly assessment during the entire study).

II-A Measurement, Collection and Analysis of Efficacy Assessment Parameters

Digestive Symptom (Borborygmi/Rumbling Stomach)

The frequency of individual digestive symptom (borborygmi/rumbling stomach) has been evaluated weekly with a 5-point Likert scale that ranges from 0 (never) to 4 (every day of the week). This assessment has been done throughout the study from the entry of the subject into the study to the last visit. It has been asked each time to the subject to evaluate the frequency of each symptom over the previous 7 days.

A composite score has been calculated from these information.

It was chosen to follow the frequency of digestive symptoms instead of intensity/severity, which is usually followed in trials on functional bowel disorders. This seems more relevant as the intensity or severity of digestive symptoms is low in a global population without diagnosis of gastrointestinal disorders.

II-B Statistics

Descriptive Statistics

Distribution of study parameters and covariants (age, body mass index, stool frequency . . . ) has been summarised depending on the type of variable in question together with a description of the number of subjects and of the number of missing data (where relevant).

The following descriptive statistics are given for each type of variable:

Qualitative data: number and frequency.

Ordinal qualitative data: median, quartiles, number of occurrences and frequency.

Continuous data: number, mean, standard deviation of the variable (SD), standard error of the mean (SEM), range (minimum-maximum), median, quartiles and confidence intervals if possible.

Summary tables of study parameters must be prepared across all subjects and at least by level of principal effects (product, time . . . ).

Statistical Analysis

Baseline data has been collected before product consumption:

The baseline value for digestive symptoms is the median value based on the two weeks before product consumption.

For qualitative parameter, the comparison between groups is performed at each measurement time with a Chi-2 test with continuity correction or by a Fisher exact test in case of violation of chi-2 test assumption on size of expected frequencies.

For ordinal data, the comparison between groups is performed by a Generalised linear model to take into account the ordinal property of the parameters. For repeated measures, mixed multi level modelling and/or Generalised Estimating Equation analysis may also be performed if necessary as a secondary analysis.

For quantitative data, the distribution of study parameters is analysed. In the case of normality, analyses have been performed with a parametric analysis, otherwise with a non-parametric or distribution free analysis. Nevertheless, before the non-parametric/distribution free approach has been adopted, some variable transformation has been tried in order to find the best way to analyse the parameters using parametric tests.

Degree of Planned Statistical Significance

The statistical tests of main effects have been performed using a two-sided significance level of 5%. A significance level of between 5 and 10% is considered as indicative of a trend. Concerning the threshold of significance for the interaction effects, the level to conclude as a significant effect is 10%.

The interaction factors could be estimated if the p value is <0.05.
Evaluation Criteria
Main Investigation:
   Comparison of trends between groups over 4 weeks of product consumption in double blind.
Secondary Investigations:
   Multiple comparison if relevant
   Descriptive statistics at each time for each group

III. Results

Baseline Data

Baseline distribution of borborygmi frequency is shown in FIG. 1. More than 60% of the population presents a borborygmi frequency from 1 time per week to 2 to 3 days per week.

Figure 2:
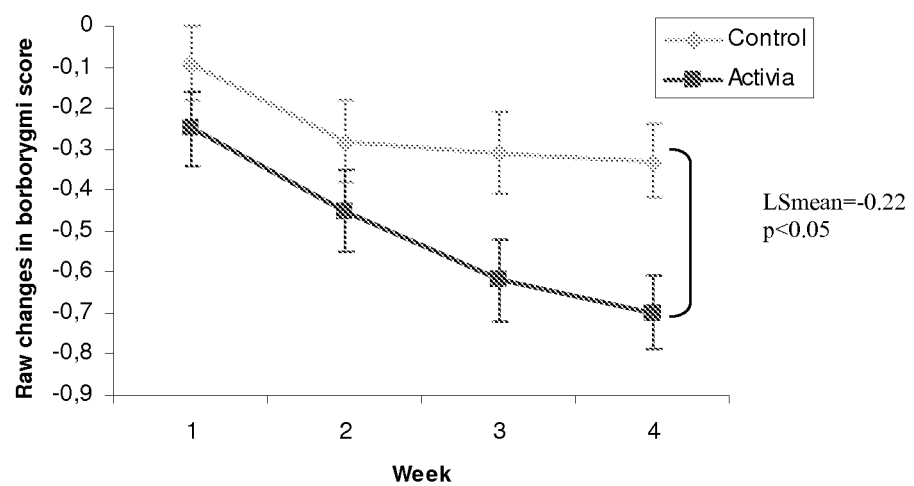
FIG. 2: Changes of borborygmi frequency score in the ITT population.

A significant reduction (mean reduction −0.22, $p<0.05$) of the borborygmi score has been shown during the 4 weeks of product consumption (FIG. 2). The highest reduction in borborygmi score is observed after 4 weeks of product consumption (Activia group=−0.70 vs Control group=−0.33; $p<0.05$).

Figure 3:
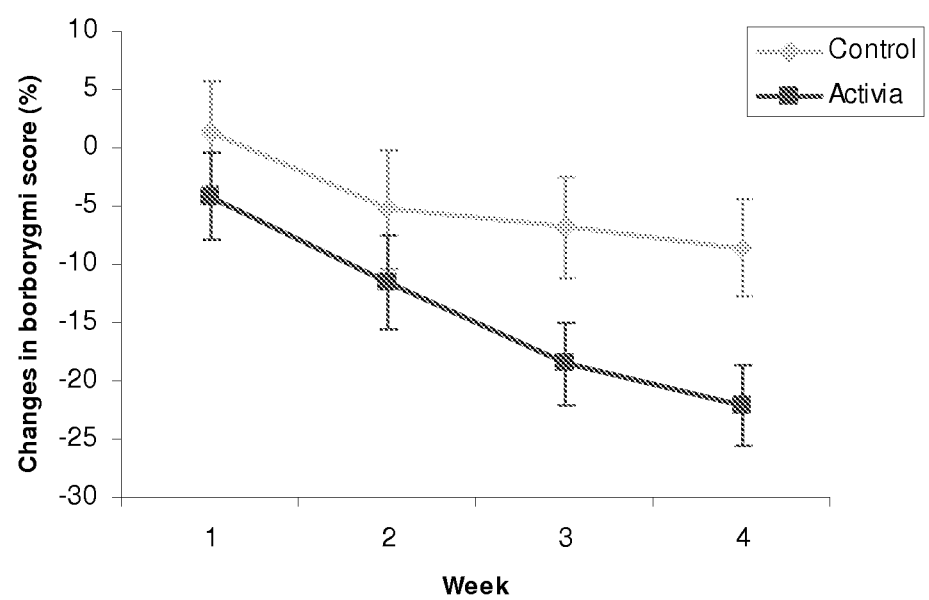
FIG. 3: Relative changes of borborygmi frequency score in the ITT population.

Relatives changes in borborygmi frequency score are shown in FIG. 3. 11% of reduction is observed after 2 weeks of product consumption (Activia group=−22% vs Control group=−5%). The higher reduction is observed after 4 weeks of product consumption (Activia group=−22% vs Control group=−9%).

REFERENCES

1. Longstreth G F, Thompson W G, Chey W D, Houghton L A, Mearin F, Spiller R. "Functional Bowel Disorders"; Gastroenterology 2006; 130 (5): 1480-91.
2. Drossman D A, Li Z, Andruzzi E et al. "US Householder survey of functional gastrointestinal disorders: prevalence, sociodemography and health impact"; Dig Dis Sci 1993, 38: 1569-1580.
3. Thompson W G. "A world view of IBS". In: Spiller R and Camilleri M, eds. "The Irritable Bowel Syndrome, Diagnosis and treatment"; WB Saunders, 2002: 17-26.
4. Longstreth G F. "Definition and classification of IBS: current consensus and controversies"; Gastroenterol Clin North Am 2005; 34: 173-187.
5. Longstreth G F, Bolus R, Naliboff B et al. "Impact of irritable bowel syndrome on patient lives: development and psychometric documentation of disease-specific measure for use in clinical trials"; Eur J Gastroenterol Hepatol 2005; 17: 411-420.
6. Wilson A, Longstreth G, Knight K et al. "Quality of life in managed care patients with irritable bowel syndrome"; Manage Care Interface 2004: 17: 24-28.
7. Spiller R, Aziz Q, Creed F, Emmanuel A, Houghton L A, Hungin P, Jones R, Kumar D, Rubin G, Trudghill N, Whorwell P J. "Guidelines for the management of irritable bowel syndrome"; Gut 2006 (in press).
8. Bougle et al. "Effect of Propionibacteria Supplementation on Fecal Bifidobacteria and Segmental Colonic Transit Time in Healthy Human Subjects"; 1999 Scand. J. Gastroenterol. 34 p144.
9. Fioramonti J, Theodorou V and Bueno L. "Probiotics: what are they? What are their effects on gut physiology?" *Best Pract Res Clin Gastroenterol* 2003; 17:711-724.
9bis. Quigley EMM and Flourié B. Probiotics and irritable bowel syndrome: a rationale for their use and an assessment of the evidence to date. *Neugastroenterol Motil* 2007; 19:166-172.
10. US 20030147858
11. Kajander et al., "clinical trial: multispecies probiotic supplementation alleviates the symptoms of irritable bowel syndrome and stabilizes intestinal microbiota", Aliment Pharmacol Ther, 2008, 27: 48-57.
12. Diplock et al. "Scientific concepts of functional foods in Europe: consensus document"; British Journal of Nutrition, 1999, 81, S1-S27
13. Houghton L A, Lea R, Agrawal A, Reilly B and Whorwell P J. "Relationship of abdominal bloating to distension in irritable bowel syndrome and effect of bowel habit"; *Gastroenterology* 2006; 131:1003-1010.
14. Kajander et al., "A probiotic mixture alleviates symptoms in irritable bowel syndrome patients: a controlled 6-month intervention"Aliment Pharmacol Ther., 2005, 22:387-394.
15. Rome III—Functional Gastrointestinal Disorders—Third edition. p 869; Drossman DA Eds, Degnon Associates, Inc. Mc lean Va.
16. Masco et al, "Polyphasic taxonomic analysis of *Bifidobacterium animalis* and *Bifidobacterium lactis* reveals relatedness at the subspecies level: reclassification of *Bifidobacterium animalis* as *Bifidobacterium animalis* subsp. *animalis* subsp. *nov.* and *Bifidobacterium lactis* as *Bifidobacterium animalis* subsp. *lactis* subsp. *Nov.*" International Journal of Systematic and Evolutionary Microbiology (2004), 54, 1137-1143.

The invention claimed is:

1. A method for decreasing borborygmi in a healthy subject, comprising the step of administering to said healthy subject at least $1 \times 10^9$ cfu of *Bifidobacterium animalis* per day during at least 15 days, wherein said administering step leads to a decrease of borborygmi in said healthy subject.

2. The method according to claim 1, wherein the decrease of borborygmi of the subject is a decrease of borborygmi frequency of at least 20%.

3. The method according to claim 1, wherein the decrease of borborygmi of the subject is a decrease of borborygmi frequency of between 20% and 50%.

4. The method according to claim 1, wherein said bacteria is chosen in the group of *Bifidobacterium animalis* subspecies *lactis* species.

5. The method according to claim 2, wherein said bacteria is chosen in the group of *Bifidobacterium animalis* subspecies *lactis* species.

6. The method according to claim 1, wherein said *Bifidobacterium animalis* is *Bifidobacterium animalis* subspecies *lactis* deposited under the number CNCM I-2494.

7. The method according to claim 2, wherein said *Bifidobacterium animalis* is *Bifidobacterium animalis* subspecies *lactis* deposited under the number CNCM I-2494.

8. The method according to claim 4, wherein said *Bifidobacterium animalis* is *Bifidobacterium animalis* subspecies *lactis* deposited under the number CNCM I-2494.

9. The method according to claim 1, wherein about $1.25 \times 10^{10}$ cfu of said *Bifidobacterium animalis* is administered to the subject two times per day during at least 28 days.

10. The method according to claim 2, wherein about $1.25 \times 10^{10}$ cfu of said *Bifidobacterium animalis* is administered to the subject two times per day during at least 28 days.

11. The method according to claim 4, wherein about $1.25 \times 10^{10}$ cfu of said *Bifidobacterium animalis* is administered to the subject two times per day during at least 28 days.

12. The method according to claim 6, wherein about $1.25 \times 10^{10}$ cfu of said *Bifidobacterium animalis* is administered to the subject two times per day during at least 28 days.

13. The method according to claim 1, wherein the subject's gender is female.

14. The method according to claim 1, wherein said *Bifidobacterium animalis* is administered in the form of a dairy product.

15. The method according to claim 14, wherein said dairy product is a fermented dairy product.

16. The method according to claim 15, wherein the fermented dairy product comprises *Lactobacillus bulgaricus* and/or *Streptococcus thermophilus*.

17. The method according to claim 15, wherein the fermented dairy product is a yogurt.

* * * * *

UNITED STATES PATENT AND TRADEMARK OFFICE
CERTIFICATE OF CORRECTION

PATENT NO. : 8,715,644 B2
APPLICATION NO. : 12/993900
DATED : May 6, 2014
INVENTOR(S) : Denis Guyonnet et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this
Twenty-fourth Day of March, 2015

Michelle K. Lee
*Director of the United States Patent and Trademark Office*